(12) United States Patent
Tsai

(10) Patent No.: US 7,175,431 B2
(45) Date of Patent: Feb. 13, 2007

(54) WATER GUIDING MECHANISM OF TEETH CLEANING MACHINE

(76) Inventor: Chih-I Tsai, No. 3, 4F-11, Wu-Qiang First Rd., Xin-Zhuang, Taipei Xian (TW)

( * ) Notice: Subject to any disclaimer, the term of this patent is extended or adjusted under 35 U.S.C. 154(b) by 172 days.

(21) Appl. No.: 11/024,822

(22) Filed: Dec. 30, 2004

(65) Prior Publication Data

US 2006/0147878 A1   Jul. 6, 2006

(51) Int. Cl.
*A61C 1/07* (2006.01)

(52) U.S. Cl. ............................................. 433/86

(58) Field of Classification Search ............... 433/80, 433/86, 119

See application file for complete search history.

(56) References Cited

U.S. PATENT DOCUMENTS 3,956,826 A * 5/1976 Perdreaux, Jr. ............ 433/86
4,330,278 A * 5/1982 Martin ...................... 433/81
4,370,131 A * 1/1983 Banko ....................... 433/86
4,961,698 A * 10/1990 Vlock ........................ 433/86
5,431,565 A * 7/1995 Euvrard .................... 433/119
5,749,727 A * 5/1998 Dao et al. ................. 433/119

* cited by examiner

*Primary Examiner*—Ralph A. Lewis
(74) *Attorney, Agent, or Firm*—Birch, Stewart, Kolasch & Birch, LLP

(57) ABSTRACT

A water guiding mechanism of teeth cleaning machine comprising a center shaft, a plastic base and an 'O' shape ring, the major character as following: a stainless-steel head is installed on the front of the center shaft, a bend is on the center of the stainless-steel head, a sleeve in on the front inner side of the plastic base, a silicon sleeve is on the front brink of the sleeve, the silicon sleeve wraps the backside of the stainless-steel head and around the bend, a compression chamber is installed between the back half of the silicon sleeve and the stainless-steel head; based on the structure described above, the compression chamber of the silicon sleeve is applied to guide and compress water, the stainless tip can aim upward, and achieve the effect to minimize the possibility to have water spray on patients' faces.

1 Claim, 5 Drawing Sheets

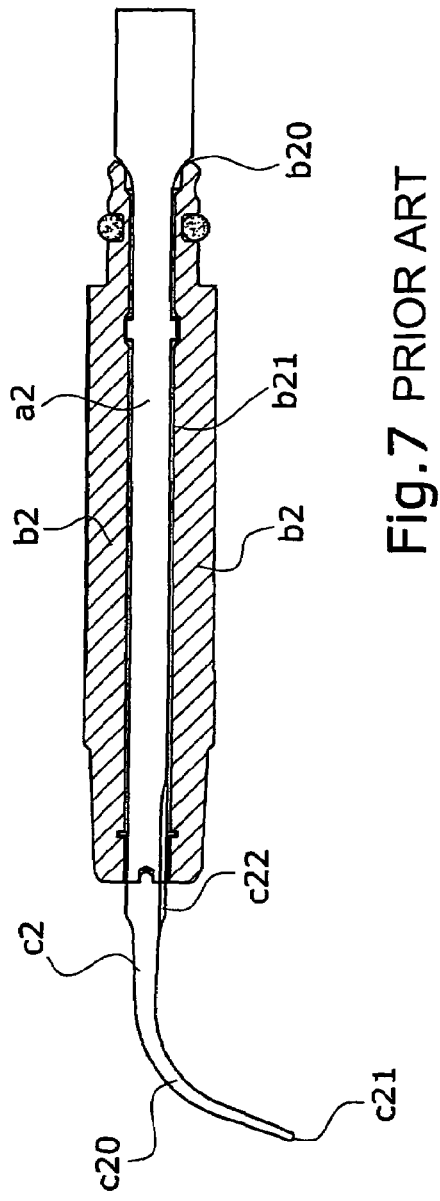
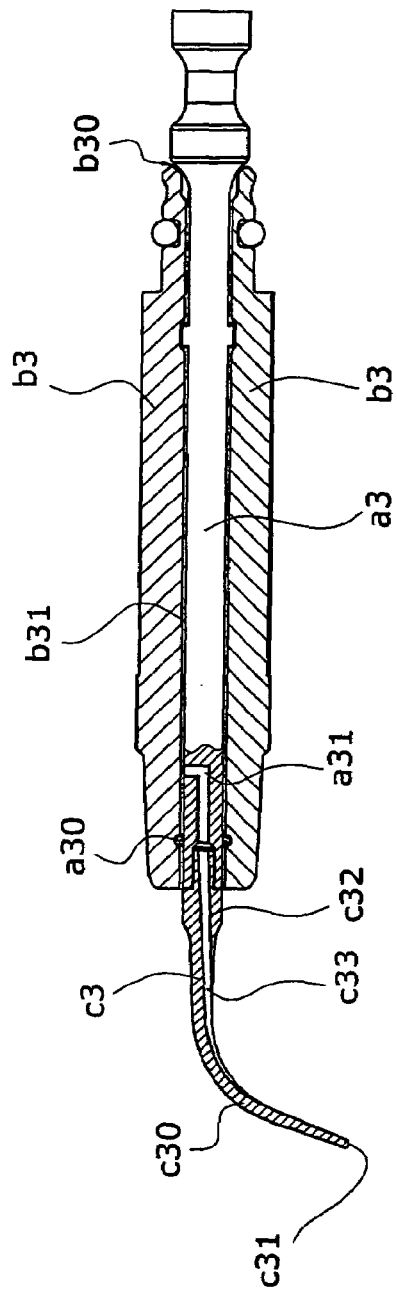
Fig.7 PRIOR ART
Fig.8 PRIOR ART

WATER GUIDING MECHANISM OF TEETH CLEANING MACHINE

BACKGROUND OF THE INVENTION

I. Field of the Invention

This invention relates generally to a water guiding mechanism and, more specifically, to a water guiding mechanism of teeth cleaning machine that tests the high frequency transmission IC's, the present invention achieves lower manufacturing cost, better contact of IC pins and the contact parts of the test connectors to reduce contact impedance, magnetic wave interference for better high frequency transmission effect.

II. Description of the Prior Art

Heretofore, it is known that teeth cleaning can remove tartar, stains and spots of teeth to make the surface of teeth smooth and easy to clean, reduce the possibility of periodontal disease. The regular teeth cleaning machine have a cleaning head, as shown in FIG. 5, the cleaning head consists of a center shaft a1 and a metal base b1, the center shaft a1 is installed inside the metal base b1, a stainless-steel head c1 is on the front of the center shaft a1, a bend c10 is in the middle of the stainless-steel head c1.

Based on above structure, while application, the center shaft a1 generates high-speed vibration; the vibration is transmitted to the tip c11 of the stainless-steel head c1, dentists scrape off teeth tartar by the high-speed vibration of the tip c11; however the high-speed vibration generates high temperature, sending water to cool down the stainless-steel tip c11 is essential and important task; the known prior art has three different kinds of types, referring to FIG. 5, the cooling mechanism of the first type is to have a water inlet hole b10 behind the metal base b1, a stainless water pipe d1 is on top of the metal base b1 and the stainless-steel head c1, a water outlet d10 is on the front of the stainless water pipe d1, the water outlet d10 faces the bend c10 of the stainless-steel head c1.

Based on above description, while the known prior teeth cleaner is in application, the cooling water flows in from the water inlet b10, goes through the stainless water pipe d1 and sprays out from the water outlet d10, cooling water sprays directly on the bend c10 of the stainless-steel head c11 to cool down the stainless-steel tip c11.

However, referring to FIG. 5 and FIG. 6, cooling water flows out from the stainless water pipe d1, the swing of the stainless water pipe d1 makes the water outlet d10 deviate away from the center of the bend c10, the water sprayed out from the water outlet d10 cannot flow to the stainless tip c11, such might cause teeth damage by the overheating of the stainless tip c11; the gap between the stainless water pipe d1 and the metal base b1 might have germs and bacteria; the stainless material of the stainless water pipe d1 is not easy to tear off for cleaning and disinfection, that might potentially spread disease.

In order not to have difficulty for cleaning and disinfection problem, a second type of prior teeth cleaner applies a side ditch to replace the stainless water pipe d1 described above; referring to FIG. 7, such known prior art consists of a center shaft a2, a plastic base b2 and a stainless-steel head c2; the stainless-steel head c2 is installed on the front of the center shaft a2, a bend c20 is on the center of the stainless-steel head c2, the center shaft a2 is inside the plastic base b2; a main water path b21 is between the lower side of the center shaft a2 and the stainless-steel head c2, a side ditch c22 is on the junction of the center shaft a2 and the stainless-steel head c2, the side ditch c22 interlinks the main water path b21, a water inlet hole b20 is on the back of the plastic base b2, the water inlet hole b20 interlinks the main water path b21; based on above description, when water enters from water inlet hole c22, goes through main water path b21 to the side ditch c22 and sprays out from the side ditch c22, water sprayed from the side ditch c22 should flow through the surface of the stainless-steel head c2 to the stainless tip c21.

However, when water sprays out from the side ditch c22 of the known second type teeth cleaner, since the bend c20 is on the center of the stainless-steel head c2, water from the side ditch c22 cannot follow the curve of the bend c20 completely, partial of the water cannot flow from the bend c20 will come off the surface of the stainless-steel head c2 and spray all directions, the come-off water might sprays on patients' faces; the side ditch c22 is installed on the lower portion of the junction of the of the center shaft a2 and the stainless-steel head c2, while cleaning the teeth on the palate, water might not go upward and reach the stainless tip c21.

In order to prevent the side ditch c22 installed between the junction of the center shaft a2 and the stainless-steel head c2 described above from spraying water on patients' faces, a third type teeth cleaner is to have a water path inside the center shaft and the stainless-steel head; referring to FIG. 8, the known third type teeth cleaner consists of a center shaft a3, a plastic base b3, a front 'O' shape ring a30 and the stainless-steel head c3, the stainless-steel head c2 is on the front of the center shaft a3, a bend c30 is on the center of the stainless-steel head c3, the center shaft a3 is installed inside the plastic base, a main water path b31 is between the upper side of the center shaft a3 and the plastic base b3, the front 'O' shape ring a30 is installed between the front side of the center shaft a3 and the plastic base b3, a water inlet hole b30 is on the back of the center shaft a3 and the plastic base b3, a front end water path c32 is inside the stainless-steel head c3, a back end water path a31 is on the front of the center shaft a3; the back of the back end water path a31 interlinks the main water path b31, the front of the back end water path a31 interlinks back of the front end water path c32, a water outlet c33 of the front end water path c32 is on the bend c30 of the stainless-steel head c3; based on above structure, water enters from the water inlet hole b30, reaches main water path b31, then enters the back end water path a31 by the block of the front 'O' shape ring a30, water in the back end water path a31 flows into the front end water path c32 and sprays out from the water outlet c33; the water outlet c33 locates close to the bend c30, water from the water outlet c33 can spray directly to the stainless-steel head c31.

However, the front end water path c32 of the third type teeth cleaner is installed inside the stainless-steel head c3, the front end water path c32 is drilled out inside the stainless-steel head c3, the strength of the stainless-steel head c3 is not so strong, the stainless-steel head c3 might break by the strike of the high speed vibration, the broken stainless-steel head c3 might enter patients' body during cleaning, such will cause dentists and patients tremendous persecution.

SUMMARY OF THE INVENTION

It is therefore a primary object of the invention to provide a water guiding mechanism of teeth cleaning machine that minimizes the possibility to spray water on patients' faces, and can be sterilized by high temperature and high pressure to reduce cross-infection among patients.

In order to achieve the objective set forth, a water guiding mechanism of teeth cleaning machine in accordance with the present invention comprises a center shaft, a plastic base and an 'O' shape ring, the major character as following: a stainless-steel head is installed on the front of the center shaft, a bend is on the center of the stainless-steel head, a sleeve in on the front inner side of the plastic base, a silicon sleeve is on the front brink of the sleeve, the silicon sleeve wraps the backside of the stainless-steel head and around the bend, a compression chamber is installed between the back half of the silicon sleeve and the stainless-steel head, a water outlet hole is between the front of the silicon sleeve and the stainless-steel head.

Based on the structure described above, the compression chamber of the silicon sleeve is applied to guide and compress water, water sprays out from the water outlet hole has stronger pressure to compensate gravity, while the stainless tip aim upward, water from water outlet hole can reach the stainless tip to cool down, water spraying from the water outlet hole will not spread out from the bend that minimizes the possibility to have water spray on patients' faces.

BRIEF DESCRIPTION OF THE DRAWINGS

The accomplishment of the above-mentioned object of the present invention will become apparent from the following description and its accompanying drawings which disclose illustrative an embodiment of the present invention, and are as follows:

FIG. 7 is a cross-sectional view of the second prior art.

FIG. 8 is a cross-sectional view of the third prior art.

DESCRIPTION OF THE PREFERRED EMBODIMENT

Figure 1:
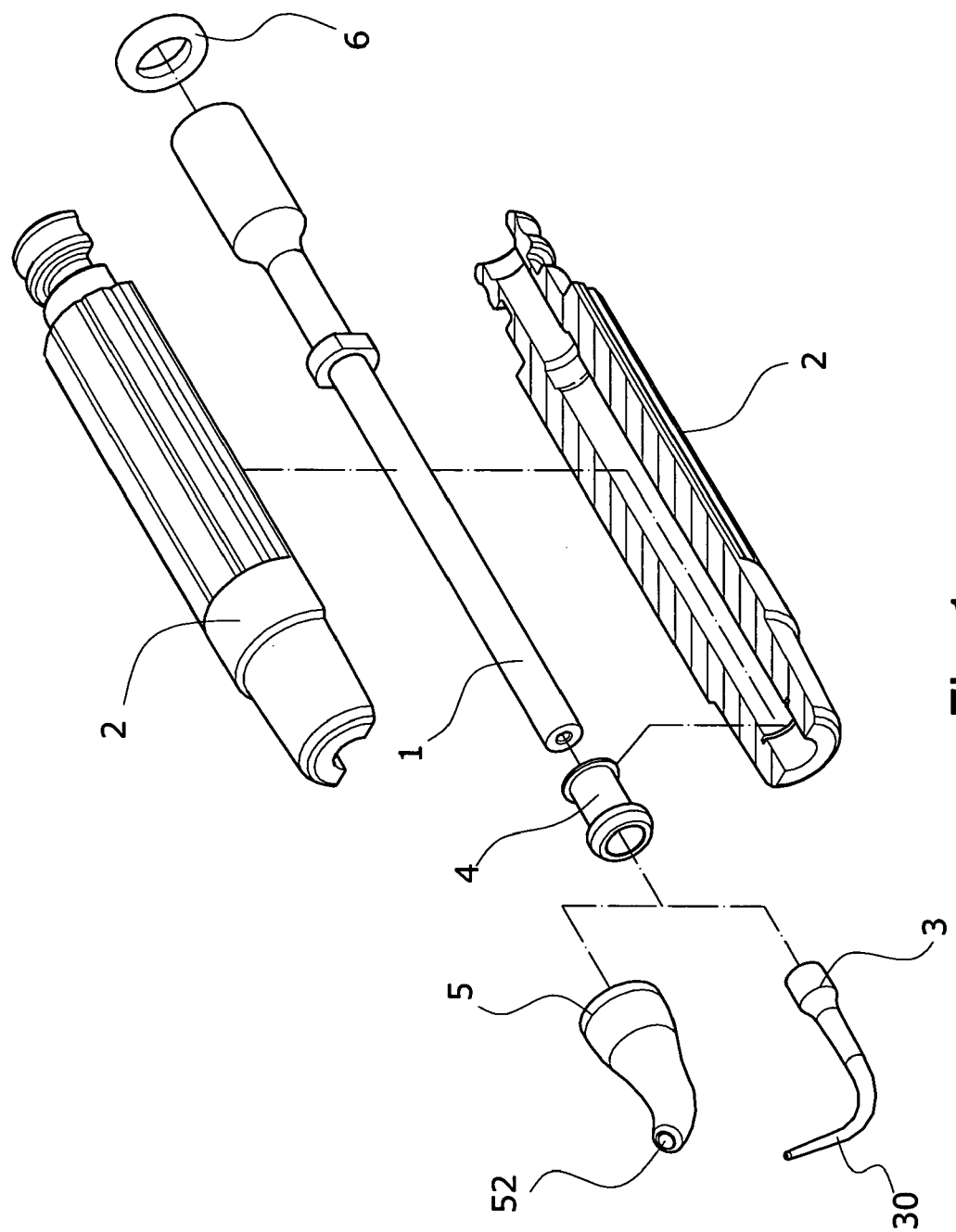
FIG. 1 is an assembly view of the present invention.
Figure 2:
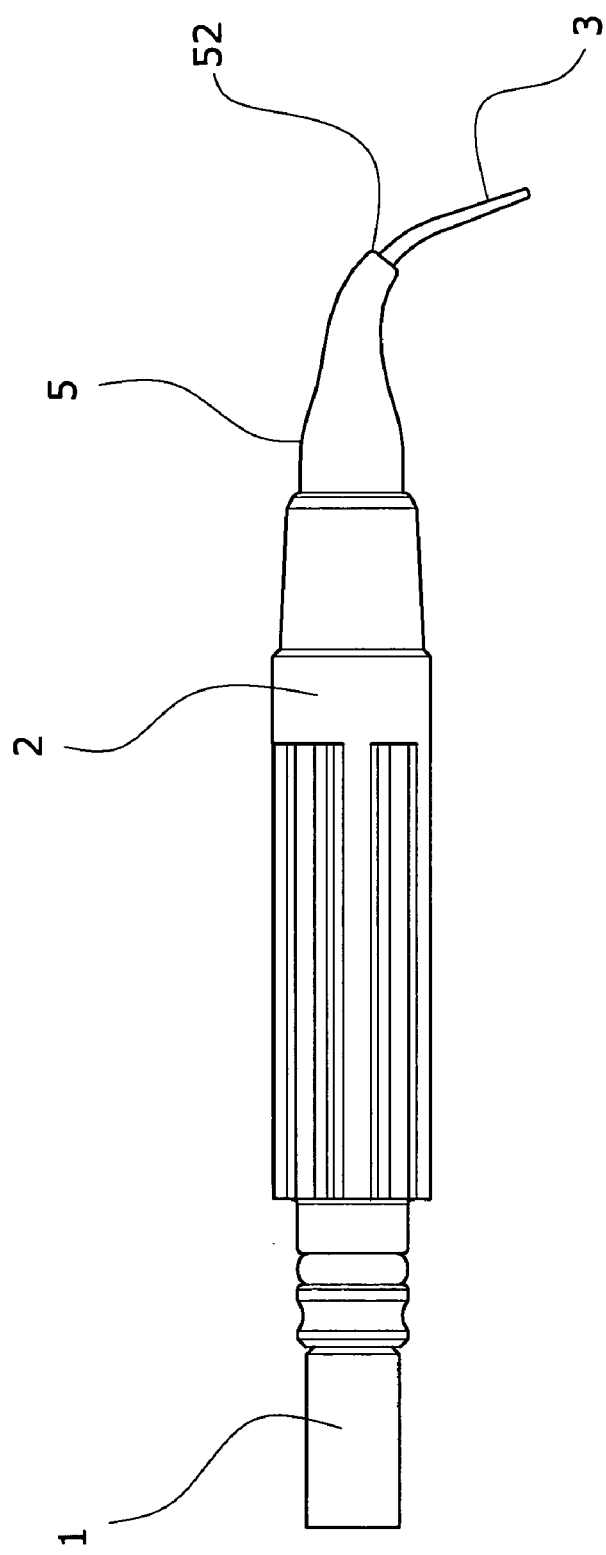
FIG. 2 is a cross-sectional view of the present invention.
Figure 3:
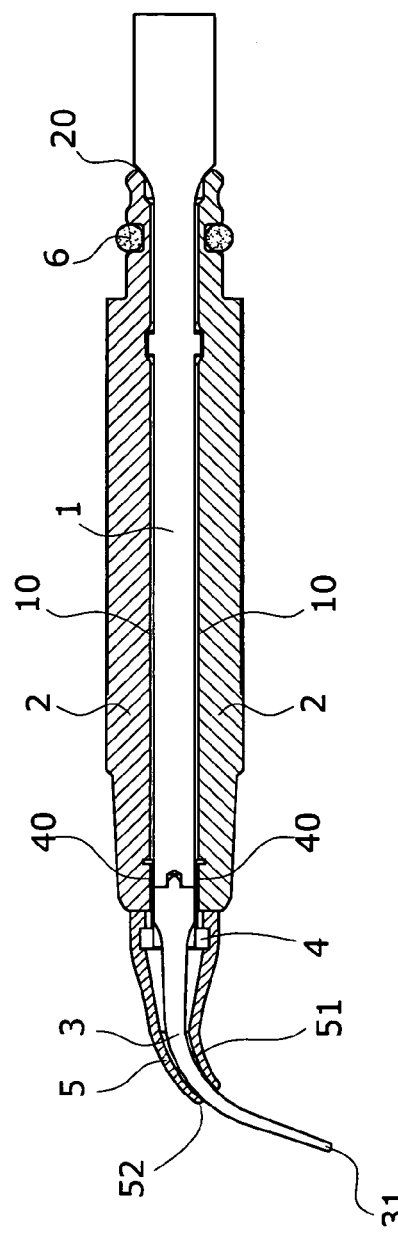
FIG. 3 is a perspective view of the present invention.
Figure 4:
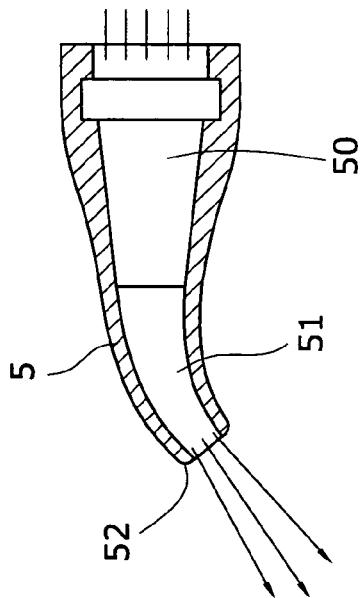
FIG. 4 is a cross-sectional view of a further embodiment of the present invention.
Figure 5:
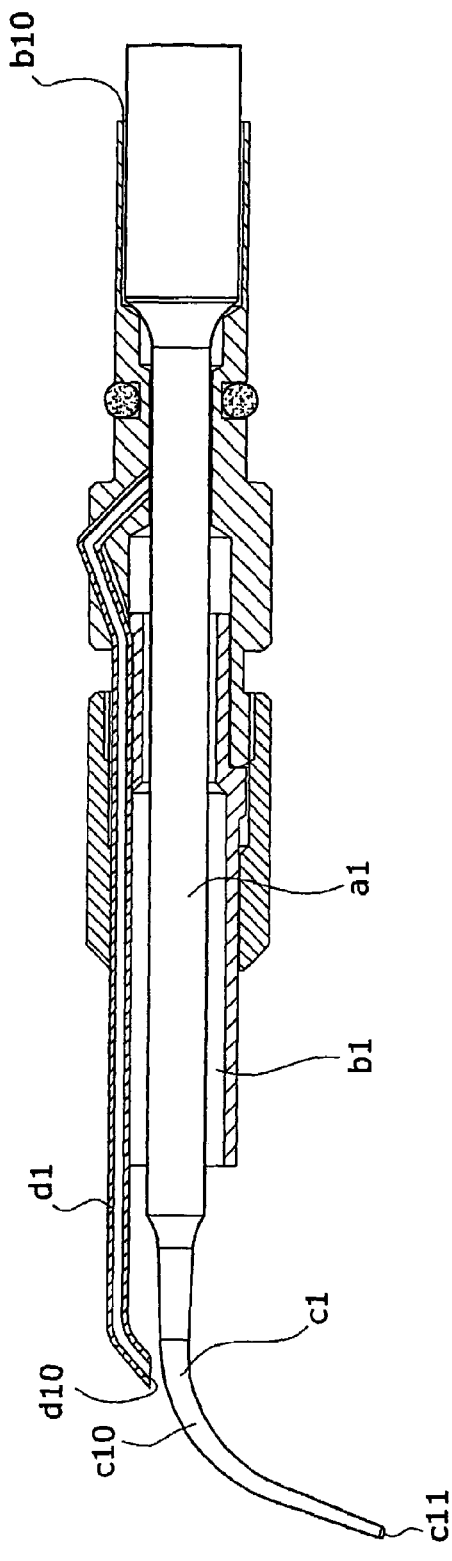
FIG. 5 is a cross-sectional view of the first prior art.
Figure 6:
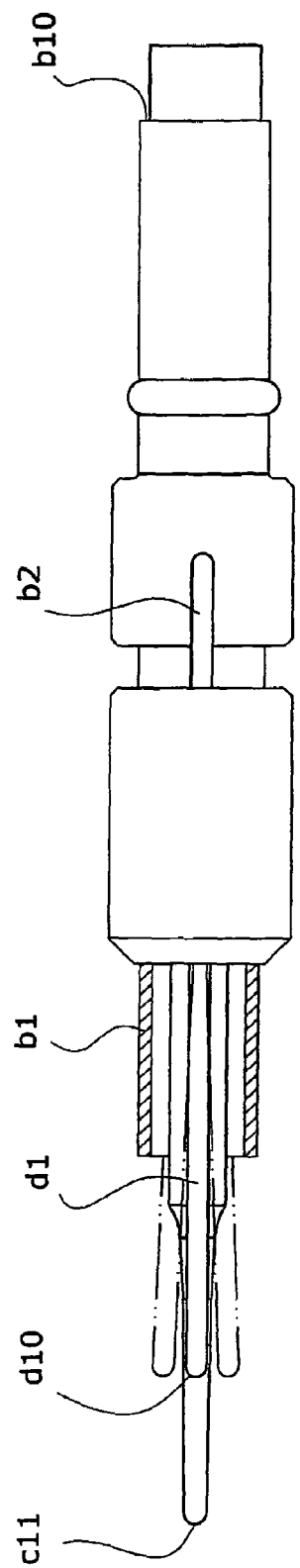
FIG. 6 is an application view of the first prior art.

Referring to FIG. 1 to FIG. 4, the present invention comprises a center shaft 1, a plastic base 2 and an 'O' shape ring 6, a water duct 10 is between the center shaft 1 and the plastic base 2, a water inlet hole 20 is on the back of the plastic base 2. The function of each component is described as following:

A stainless-steel head 3 is installed on the front of the center shaft 1, a bend 30 is on the center of the stainless-steel head 3, a sleeve 4 in on the front inner side of the plastic base 2, the front of the sleeve 4 stretches out front the plastic base 2 for a certain distance, a water outlet duct 40 is installed among the sleeve 4, the center shaft 1 and the stainless-steel head 3, a silicon sleeve 5 is on the front brink of the sleeve 4.

The silicon sleeve 5 wraps the backside of the stainless-steel head 3 and around the bend 30, a compression chamber 50 is installed between the back half of the silicon sleeve 5 and the stainless-steel head 3, a flow guiding path 51 is between the front half of the silicon sleeve 5 and the stainless-steel head 3, the flow guiding path 51 surrounds the outside of the bend 30 with the same curve as the bend 30, a water outlet hole 52 is between the front of the silicon sleeve 5 and the stainless-steel head 3.

Based on the structure described above and while application, water enters from the water inlet hole 20, flows through the water duct 10 and reaches the water outlet duct 40, then goes through the compression chamber 50, follows the flow guiding path 51 to the water outlet hole 52, finally sprays out from the water outlet hole 52, the spraying water flows along the surface of the stainless-steel head 3, reaches the stainless tip 31 and sprays on patients' teeth.

Based on above description, the inner diameters of the compression 50 and the flow guiding path 51 shrink from back to front, water with pressure enters from a larger pipe into a smaller pipe, the smaller the diameter, the larger the pressure; water flows from the compression chamber 50 to the flow guiding path 51 will have larger pressure, the stainless tip 31 can be applied upward, water from the water outlet hole 52 also flows up to cool the stainless tip 31 down; since the silicon sleeve 5 wraps around the bend externally, the water guiding path 51 between the front half of the silicon sleeve 5 and the stainless-steel head 3 have the same curve as the bend 30; the water guiding path 51 between the silicon sleeve 5 and the stainless-steel head 3 together with the compression chamber 50 can guide water to have water spray from the water outlet hole 52 and aim at the stainless tip 31, water spraying from the water outlet hole 52 will not spread out from the bend 30 that minimizes the possibility to have water spray on patients' faces.

While a preferred embodiment of the invention has been shown and described in detail, it will be readily understood and appreciated that numerous omissions, changes and additions may be made without departing from the spirit and scope of the invention.

What is claimed is:

1. A water guiding mechanism of teeth cleaning machine comprising:

a center shaft, a plastic base and an 'O' shape ring, a water duct is between the center shaft and the plastic base, a water inlet hole is on the back of the plastic base;

a stainless-steel head is installed on the front of said center shaft, a bend is on the center of said stainless-steel head, a sleeve is on the front inner side of said plastic base, the front of said sleeve stretches out front said plastic base for a certain distance, a water outlet duct is installed along said sleeve, said center shaft and said stainless-steel head, a silicon sleeve is on the front brink of the sleeve;

said silicon sleeve wraps the backside of said stainless-steel head and around said bend, a compression chamber is installed between the back half of said silicon sleeve and said stainless-steel head, a flow guiding path is between the front half of said silicon sleeve and said stainless-steel head, said flow guiding path surrounds the outside of said bend with the same curve as said bend, a water outlet hole is between the front of said silicon sleeve and said stainless-steel head.

* * * * *